United States Patent
Lim et al.

(10) Patent No.: US 9,305,345 B2
(45) Date of Patent: Apr. 5, 2016

(54) SYSTEM AND METHOD FOR IMAGE BASED INSPECTION OF AN OBJECT

(71) Applicant: General Electric Company, Schenectady, NY (US)

(72) Inventors: Ser Nam Lim, Niskayuna, NY (US); Jose Abiel Garza, McAllen, TX (US); David Scott Diwinsky, Cincinnati, OH (US); Li Guan, Clifton Park, NY (US); Shubao Liu, Niskayuna, NY (US); Xingwei Yang, Bellevue, WA (US); Jens Rittscher, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 62 days.

(21) Appl. No.: 14/260,624

(22) Filed: Apr. 24, 2014

(65) Prior Publication Data

US 2015/0310604 A1    Oct. 29, 2015

(51) Int. Cl.

| | |
|---|---|
| G06K 9/00 | (2006.01) |
| G06T 7/00 | (2006.01) |
| G06T 17/00 | (2006.01) |
| G06K 9/52 | (2006.01) |
| H04N 17/00 | (2006.01) |
| G01N 21/88 | (2006.01) |

(52) U.S. Cl.
CPC ............... *G06T 7/0004* (2013.01); *G06K 9/52* (2013.01); *G06T 7/001* (2013.01); *G06T 7/0018* (2013.01); *G06T 7/0032* (2013.01); *G06T 7/0046* (2013.01); *G06T 17/00* (2013.01); *H04N 17/00* (2013.01); *G01N 2021/8896* (2013.01); *G06T 2207/30164* (2013.01)

(58) Field of Classification Search
None
See application file for complete search history.

(56) References Cited

U.S. PATENT DOCUMENTS

| | | | |
|---|---|---|---|
| 4,995,087 A | | 2/1991 | Rathi et al. |
| 5,026,967 A | * | 6/1991 | Bell et al. ................. 219/121.64 |
| 5,848,115 A | | 12/1998 | Little et al. |
| 8,244,025 B2 | * | 8/2012 | Davis et al. ................... 382/154 |
| 8,368,749 B2 | | 2/2013 | Lambdin et al. |
| 8,528,317 B2 | | 9/2013 | Gerez et al. |

(Continued)

FOREIGN PATENT DOCUMENTS

| | | |
|---|---|---|
| DE | 102012014937 A1 | 4/2013 |
| DE | 102012003256 A1 | 8/2013 |

(Continued)

OTHER PUBLICATIONS

Pai et al., "Automated Visual Inspection of Aircraft Engine Combustor Assemblies", Robotics and Automation Proceedings, 1986 IEEE International Conference on (vol. 3), pp. 1919-1924.

(Continued)

*Primary Examiner* — Aaron W Carter
(74) *Attorney, Agent, or Firm* — John P. Darling

(57) ABSTRACT

A method for image based inspection of an object includes receiving an image of an object from an image capture device, wherein the image includes a representation of the object with mil-level precision. The method further includes projecting a measurement feature of the object from the image onto a three-dimensional (3D) model of the object based on a final projection matrix; determining a difference between the projected measurement feature and an existing measurement feature on the 3D model; and sending a notification including the difference between the projected measurement feature and the existing measurement feature.

17 Claims, 7 Drawing Sheets

(56) References Cited

U.S. PATENT DOCUMENTS

| | | | |
|---|---|---|---|
| 8,666,119 B1* | 3/2014 | Mallet et al. | 382/107 |
| 2005/0068552 A1* | 3/2005 | Kimura | 358/1.9 |
| 2006/0140473 A1 | 6/2006 | Brooksby et al. | |
| 2007/0269080 A1* | 11/2007 | Hamanaka | 382/106 |
| 2008/0266416 A1* | 10/2008 | Kobayashi | 348/222.1 |
| 2008/0270027 A1* | 10/2008 | Stecko et al. | 701/214 |
| 2010/0030849 A1* | 2/2010 | Miyamoto et al. | 709/203 |
| 2010/0232683 A1* | 9/2010 | Fujieda et al. | 382/154 |
| 2011/0176721 A1 | 7/2011 | McAfee et al. | |
| 2011/0206274 A1* | 8/2011 | Tateno et al. | 382/154 |
| 2011/0267428 A1* | 11/2011 | George et al. | 348/46 |
| 2012/0121135 A1* | 5/2012 | Kotake et al. | 382/103 |
| 2012/0262455 A1* | 10/2012 | Watanabe et al. | 345/420 |
| 2012/0320053 A1 | 12/2012 | Miyatani | |
| 2013/0076865 A1* | 3/2013 | Tateno et al. | 348/46 |
| 2013/0108116 A1* | 5/2013 | Suzuki et al. | 382/106 |
| 2013/0113913 A1 | 5/2013 | Scheid et al. | |
| 2013/0113915 A1 | 5/2013 | Scheid et al. | |
| 2013/0148875 A1 | 6/2013 | Brooksby et al. | |
| 2013/0208948 A1* | 8/2013 | Berkovich et al. | 382/103 |
| 2013/0235033 A1* | 9/2013 | Kim et al. | 345/419 |
| 2013/0271577 A1* | 10/2013 | Watanabe et al. | 348/46 |
| 2014/0232857 A1 | 8/2014 | Jahnke et al. | |
| 2015/0015582 A1* | 1/2015 | Kaiser et al. | 345/427 |
| 2015/0016704 A1* | 1/2015 | Weese et al. | 382/131 |
| 2015/0138236 A1* | 5/2015 | Koga | 345/633 |

FOREIGN PATENT DOCUMENTS

| | | |
|---|---|---|
| EP | 2589925 A1 | 5/2013 |
| WO | 2012172320 A1 | 12/2012 |

OTHER PUBLICATIONS

Mannan, "3D Imaging of Turbine Blade for Comparative Deviation Analysis between Ideal Part Designs to As Built Part", Thesis submitted, Rensselaer Polytechnic Institute Hartford, CT, Dec. 2009, 45 Pages.

Wang et al., "Aeroplane Engine Blade Edge Reconstruction Based on Non-Uniform B-Spine Wavelet Algorithm", 2011 International Conference on System Science, Engineering Design and Manufacturing Informatization, (vol. 1), 2011, pp. 12-15.

Ricardi et al., "A Novel Technique for Feature-Based Aircraft Identification From High Resolution Airborne ISAR Images", IGARSS 2012, pp. 2082-2085.

European Search Report and Written Opinion issued in connection with corresponding EP Application No. 15164913.4-1558 dated Sep. 24, 2015.

* cited by examiner

SYSTEM AND METHOD FOR IMAGE BASED INSPECTION OF AN OBJECT

BACKGROUND

The technology disclosed herein generally relates to an image based inspection of an object. More specifically, the subject matter relates to systems and methods to inspect an object based on an image that includes a representation of the object with mil-level precision.

Objects, for example, an aviation engine component, a gas turbine component, and the like, need to be inspected due to strict regulatory and operational requirements. For example, in the aviation industry, the Federal Aviation Administration requires that the dimensions of aviation engine components meet the necessary specifications with a high level of precision. Currently, such objects are inspected manually using hard fixtures that are built to the shape of a template object. In such methods, an inspector places the object into the hard fixture and determines a discrepancy in the object's dimensions using, for example, a dial caliper. Such methods are time consuming and expensive due to the cost of custom building hard fixtures for every object that needs to be inspected.

Thus, there is a need for an enhanced system and method for inspection of an object.

BRIEF DESCRIPTION

In accordance with one aspect of the present technique, a method includes receiving an image of an object from an image capture device, wherein the image includes a representation of the object with mil-level precision. The method further includes projecting a measurement feature of the object from the image onto a three-dimensional (3D) model of the object based on a final projection matrix. The method further includes determining a difference between the projected measurement feature and an existing measurement feature on the 3D model. The method also includes sending a notification including the difference between the projected measurement feature and the existing measurement feature.

In accordance with one aspect of the present system, a system includes a communication module configured to receive an image of an object from an image capture device, wherein the image includes a representation of the object with mil-level precision. The system further includes a back-projection module configured to project a measurement feature of the object from the image onto a 3D model of the object based on a final projection matrix and determine a difference between the projected measurement feature and an existing measurement feature on the 3D model. The system further includes a notification module configured to send a notification including the difference between the projected measurement feature and the existing measurement feature.

In accordance with another aspect of the present technique, a computer program product encoding instructions is disclosed. The instructions when executed by a processor cause the processor to receive an image of an object from an image capture device, wherein the image includes a representation of the object with mil-level precision. The instructions further cause the processor to project a measurement feature of the object from the image onto a 3D model of the object based on a final projection matrix. The instructions further cause the processor to determine a difference between the projected measurement feature and an existing measurement feature on the 3D model. The instructions also cause the processor to send a notification including the difference between the projected measurement feature and the existing measurement feature.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Figure 1:
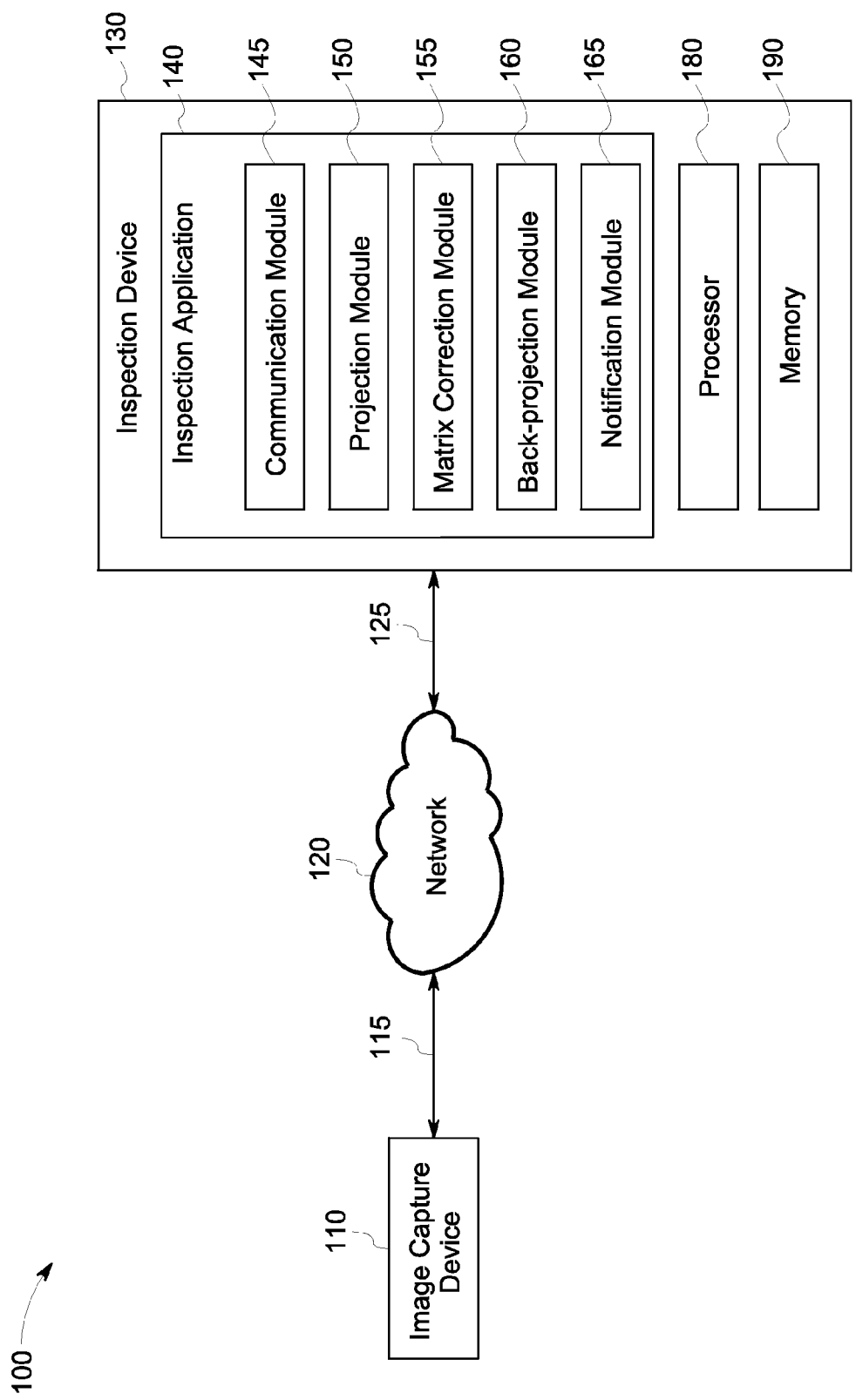
FIG. 1 is a block diagram illustrating an example of a system for image based inspection of an object.

A system and method for an image based inspection of an object is described herein. The object may include any type of object that may be perceived by the senses, for example, a component of an aviation engine, a gas turbine, a wind turbine blade, a sensor, and the like. FIG. 1 illustrates a block diagram of some implementations of a system 100 configured to inspect an object based on an image that includes a representation of the object. The system 100 includes an image capture device 110 and an inspection device 130 that are communicatively coupled via a network 120. Although the image capture device 110 and the inspection device 130 are communicatively coupled via the network 120 according to FIG. 1, the inspection device 130 may be included within the image capture device 110.

The network 120 may be a wired or wireless type, and may have any number of configurations such as a star configuration, token ring configuration, or other known configurations. Furthermore, the network 120 may include a local area network (LAN), a wide area network (WAN) (e.g., the internet), and/or any other interconnected data path across which multiple devices may communicate. In some implementations, the network 120 may be a peer-to-peer network. The network 120 may also be coupled to or include portions of a telecommunication network for sending data in a variety of different communication protocols. In some implementations, the network 120 may include Bluetooth communication networks or a cellular communications network for sending and receiving data such as via a short messaging service (SMS), a multimedia messaging service (MMS), a hypertext transfer protocol (HTTP), a direct data connection, WAP, email, or the like. While only one network 120 is shown coupled to the image capture device 110 and the inspection device 130, multiple networks 120 may be coupled to the entities.

The image capture device 110 may be any type of device that is configured to capture an image of the object, for example, a high resolution camera (e.g., a resolution of 4000× 3000 pixels), a digital single-lens reflex camera, a webcam, a mobile phone coupled with a camera, a video recorder, and the like. In some implementations, the image capture device 110 may capture an image that represents the object with mil-level precision, wherein a pixel of the image represents less than or equal to a milli-inch (i.e., a thousandth of an inch) of the object. The image capture device 110 is further configured to send the image of the object to the inspection device 130 via the network 120. The image capture device 110 is communicatively coupled to the network 120 via signal line 115. The signal line 115 is provided for illustrative purposes and represents the image capture device 110 communicating by wires or wirelessly over the network 120. Although one image capture device 110 is coupled to the network 120 in FIG. 1, a plurality of image capture devices 110 may be coupled to the network 120 to generate and send the image of the object to the inspection device 130.

Figure 2:
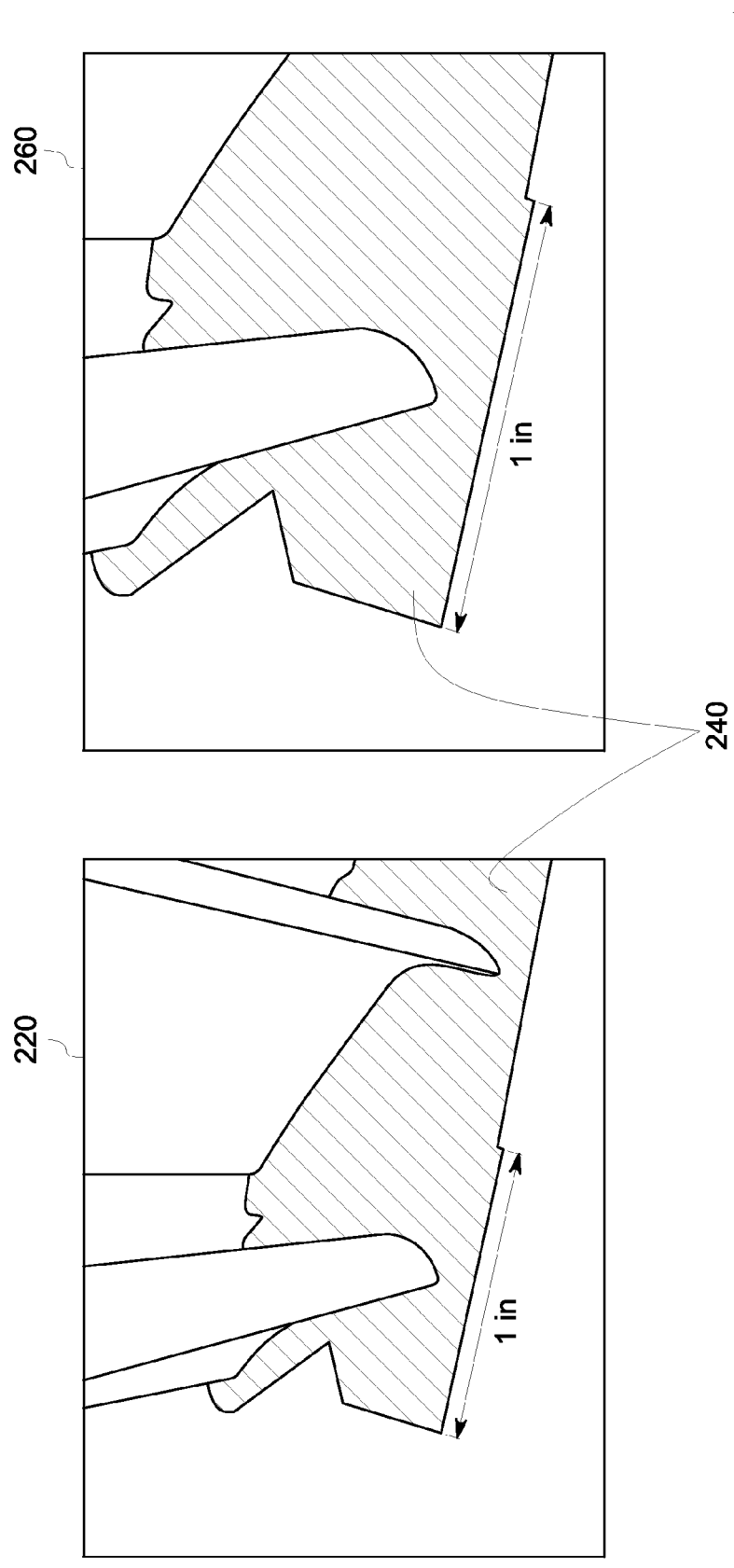
FIG. 2 is a graphical representation of example images representing an object with mil-level precision.

Referring now to FIG. 2, graphical representations of example images 220, 260 representing a surface of an object 240 (i.e., a blade) with mil-level precision are illustrated. The image 220 captured by the image capture device represents an inch of the blade's surface 240 with 1200 pixels. Thus, the image 220 represents the blade's surface 240 with a precision of 0.0008 inches (i.e., $\frac{1}{1200}$ inches). Similarly, the image 260 represents an inch of the blade's surface 240 with 2500 pixels. Thus, the image 260 represents the surface of the blade 240 with a precision of 0.0004 inches ($\frac{1}{2500}$ inches).

Referring back to FIG. 1, the inspection device 130 may be any type of device configured to inspect an object based on an image and determine a discrepancy in the object. The inspection device 130 is communicatively coupled to the network 120 via signal line 125. The signal line 125 is provided for illustrative purposes and represents the inspection device 130 communicating by wires or wirelessly over the network 120. Although one inspection device 130 is shown in FIG. 1, a plurality of inspection devices 130 may be coupled to the network 120. Additionally, although the inspection device 130 is communicatively coupled to the image capture device 110 via the network 120, the processing of the inspection device 130 may be performed within the image capture device 110. In the illustrated system 100, the inspection device 130 includes an inspection application 140, a processor 180, and a memory 190. The inspection application 140 includes a communication module 145, a projection module 150, a matrix correction module 155, a back-projection module 160, and a notification module 165. The plurality of modules of the inspection application 140, the processor 180, and the memory 190 are coupled to a bus (not shown) for communication with each other.

The processor 180 may include at least one arithmetic logic unit, microprocessor, general purpose controller or other processor arrays to perform computations, and/or retrieve data stored on the memory 190. In some implementations, the processor 180 may be a multiple core processor. The processor 180 processes data signals and may include various computing architectures including a complex instruction set computer (CISC) architecture, a reduced instruction set computer (RISC) architecture, or an architecture implementing a combination of instruction sets. In some implementations, the processing capability of the processor 180 may be limited to supporting the retrieval of data and transmission of data. In some implementations, the processing capability of the processor 180 may also perform more complex tasks, including various types of feature extraction, modulating, encoding, multiplexing, and the like. Other type of processors, operating systems, and physical configurations are also envisioned.

The memory 190 may be a non-transitory storage medium. For example, the memory 190 may be a dynamic random access memory (DRAM) device, a static random access memory (SRAM) device, flash memory or other memory devices. The memory 190 may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

The memory 190 stores data that is required for the inspection application 140 to perform associated functions. In some implementations, the memory 190 stores the modules (e.g., communication module 145, matrix correction module 155, and the like) of the inspection application 140. In some implementations, the memory 190 stores a three-dimensional (3D) model of the object, a discrepancy threshold, and the like that are defined by, for example, an administrator of the inspection device 130. The 3D model (e.g., Computer Aided Design model) represents the object using a collection of points in the 3D space (i.e., a 3D point cloud). In some implementations, the resolution of the 3D model is at least the resolution of the image of the object received from the image capture device 110. For example, if the resolution of the image received from the image capture device 110 is 4000×3000 pixels, the resolution of the object's 3D model stored in the memory 190 is equal to or higher than or equal to 4000×3000 points. The discrepancy threshold is described below in further detail with reference to the notification module 165.

The communication module 145 includes codes and routines configured to handle communications between the image capture device 110 and the modules of the inspection application 140. In some implementations, the communication module 145 includes a set of instructions executable by the processor 180 to provide the functionality for handling communications between the image capture device 110 and the modules of the inspection application 140. In some other implementations, the communication module 145 is stored in the memory 190 and is accessible and executable by the processor 180. In either implementation, the communication module 145 is adapted for communication and cooperation with the processor 180 and other modules of the inspection application 140.

In some implementations, the communication module 145 receives an image that represents an object with mil-level precision from the image capture device 110. In such implementations, the communication module 145 sends the received image to the projection module 150 and the back-projection module 160. In some other implementations, the communication module 145 receives a notification including a discrepancy in the object from the notification module 165. In such implementations, the communication module 145 sends the notification to, for example, a display device (not shown), an administrator of the inspection device 130, and the like.

The projection module 150 includes codes and routines configured to project a calibration feature from a 3D model of the object onto the image of the object and determine a projection error. A calibration feature may be any type of feature (e.g., a corner, a line, a plane, a circle, and the like) of the object that does not change and serves as a reference for the object. In some implementations, the projection module 150 includes a set of instructions executable by the processor 180 to provide the functionality for projecting a calibration feature from a 3D model of the object onto the image of the object and determine a projection error. In some other implementations, the projection module 150 is stored in the memory 190 and is accessible and executable by the processor 180. In either implementation, the projection module 150 is adapted for communication and cooperation with the processor 180 and other modules of the inspection application 140.

The projection module 150 receives the image of the object from the communication module 145. The projection module 150 retrieves the 3D model of the object from the memory 190 and projects one or more calibration features from the 3D model onto the received image of the object. In some implementations, the projection module 150 projects one or more calibration features from the 3D model onto the received image based on an initial projection matrix. The initial projection matrix may be any matrix that maps points of the object in a 3D space (i.e., 3D model) onto a two-dimensional (2D) plane (i.e., image of the object). In some implementations, the initial projection matrix is defined by, for example, an administrator of the inspection device 130 based on the assumption that the position of the object in the world (i.e., the 3D space) is fixed. The initial projection matrix includes an internal calibration matrix, an initial rotational matrix, and an initial translational matrix. The internal calibration matrix is defined based on the properties of the image capture device 110, for example, focal length, pixel resolution, the principal points, and the like. The internal calibration matrix may be defined offline using, for example, a standard camera calibration procedure. Additionally, the image capture device 110 may also be calibrated to correct non-linear distortions. The initial rotational matrix and the initial translation matrix are defined based on the rotation and the translation of the image capture device 110 in the 3D space respectively. In some other implementations, the initial rotational matrix and the initial translational matrix are defined based on the rotation and the translation of the object respectively and the assumption that the position of the image capture device 110 in the 3D space is fixed.

The projection module 150 determines a projection error between the one or more projected calibration features and the corresponding calibration features existing on the received image. In some implementations, the projection error includes a distance error between the projected calibration feature and the existing calibration feature on the received image. For example, the projection module 150 projects a corner (i.e., calibration feature) from the 3D model of the object onto the received image of the object based on the initial projection matrix. The projection module 150 calculates the number of pixels (i.e., distance error) between the projected corner and the corresponding corner of the object existing on the received image. In some other implementations, the projection error includes a distance error and an angular error between the projected calibration feature and the existing calibration feature on the received image. For example, the projection module 150 projects a line (i.e., a calibration feature) from the 3D model of the object onto the received image based on the initial projection matrix. The projection module 150 calculates the angle (i.e., angular error) between the projected line and the corresponding line of the object on the received image. The projection module 150 is further configured to send the one or more projection errors to the matrix correction module 155.

Figure 3:
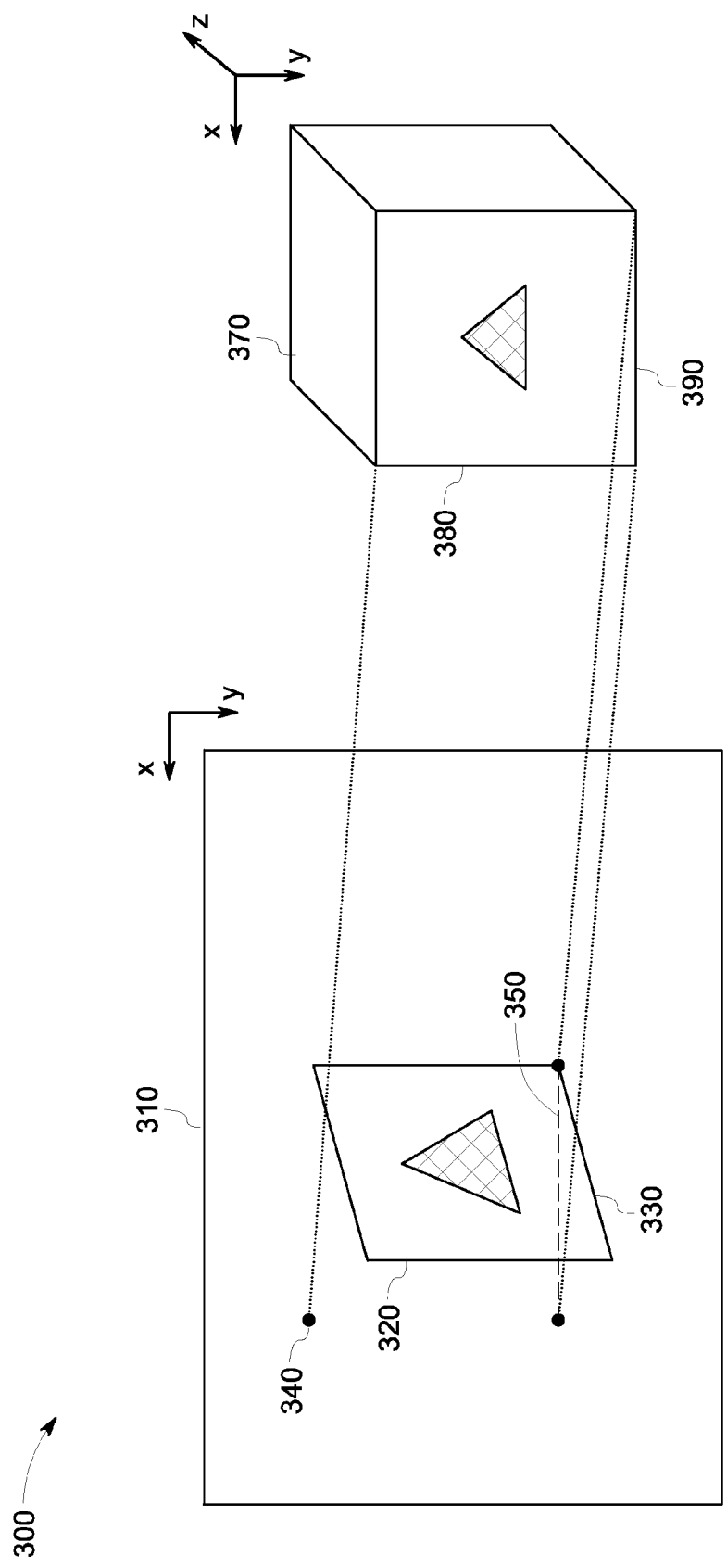
FIG. 3 is a graphical representation illustrating an example of calibration feature projections from a 3D model of an object onto an image of the object.

Referring now to FIG. 3, a graphical representation 300 of example calibration feature projections from a 3D model of an object onto an image of the object is illustrated. The graphical representation 300 includes an image 310 of an object received from an image capture device and a 3D model 370 of the object. In the illustrated example, the object is a cube including a triangular mesh on one side of the cube. The projection module projects a corner 380 and a line 390 (i.e., calibration features) from the 3D model 370 onto the image 310 of the object based on an initial projection matrix. The projection module then determines the projection error between the projected calibration features and the corresponding calibration features existing on the received image 310. In some implementations, the projection module calculates a distance error between the projected corner 340 and the existing corner 320 on the image 310. For example, the projection module calculates that the projected corner 340 is 100 pixels away along the x-axis and 80 pixels away along the y-axis from the existing corner 320 on the image 310. In another example, the projection module calculates the Euclidean distance between the projected corner 340 and the existing corner 320 on the image 310 as the distance error. The projection module may further calculate a distance error and an angular error between the projected line 350 and the existing line 330 on the image 310. For example, the projection module calculates the angular error between the projected line 350 and the existing line 330 as 35 degrees. In this example, the projection module also calculates the distance error between the projected line 350 and the existing line 330 as 250 pixels.

Referring back to FIG. 1, the matrix correction module 155 includes codes and routines configured to calculate a final projection matrix based on the initial projection matrix and the projection error. Similar to the initial projection matrix, the final projection matrix may be any matrix that maps points of the object in a 3D space (i.e., 3D model) onto a 2D plane (i.e., image of the object). The final projection matrix includes the internal calibration matrix of the initial projection matrix, a final rotational matrix, and a final translation matrix. In some implementations, the matrix correction module 155 includes a set of instructions executable by the processor 180 to provide the functionality for calculating a final projection matrix. In some other implementations, the matrix correction module 155 is stored in the memory 190 and is accessible and executable by the processor 180. In either implementation, the matrix correction module 155 is adapted for communication and cooperation with the processor 180 and other modules of the inspection application 140.

The matrix correction module 155 receives the projection error from the projection module 150. The matrix correction module 155 calculates the final projection matrix by modifying the initial projection matrix based on the projection error. The matrix correction module 155 calculates the final rotational matrix and the final translational matrix by modifying the initial rotational matrix and the initial translational matrix respectively, such that the projection error is minimized. In some implementations, the matrix correction module 155 calculates the final projection matrix such that projection error is reduced below an error threshold value. In such implementations, the error threshold value is defined by, for example, an administrator of the inspection device 130. The matrix correction module 155 calculates the final projection matrix based on optimization algorithms, for example, gradient descent algorithm, Levenburg-Marquadt non-linear optimization algorithm, and the like.

In some implementations, the matrix correction module 155 calculates the final projection matrix such that the distance error is minimized. In such implementations, the matrix correction module 155 calculates the final rotational matrix (R*) and the final translational matrix (T*) by modifying the initial rotational matrix (R) and the initial translational matrix (T) respectively, based on the minimization function:

$$\operatorname*{argmin}_{R,T} \sum_i \|\operatorname{Proj}(X_i; K, R, T) - x_i\|^2 + \sum_j \operatorname{dis}(\operatorname{Proj}(Y_j; K, R, T), L_j)^2$$

Where:
K is the internal calibration matrix;
$X_i$ is a vector representing the projected points from the 3D model;
$x_i$ is a vector representing the corresponding points existing on the 2D image;
Y is a vector representing the projected lines from the 3D model;
L is a vector representing the corresponding lines existing on the 2D image;
$\|\operatorname{Proj}(X_i; K, R, T) - x_i\|^2$ represents the distance error due to the points; and
$\operatorname{Dis}(\operatorname{Proj}(Y_j; K, R, T), L_j)^2$ represents the distance error due to the lines.

In some other implementations, the matrix correction module 155 calculates the final projection matrix such that the distance and the angular errors are minimized. In such implementations, the matrix correction module 155 calculates the final rotational matrix (R*) and the final translational matrix (T*) by modifying the initial rotational matrix (R) and the initial translational matrix (T) respectively, based on the minimization function:

$$\operatorname*{argmin}_{R,T} \sum_i \|\operatorname{Proj}(X_i; K, R, T) - x_i\|^2 + \sum_j \operatorname{dis}(\operatorname{Proj}(Y_j; K, R, T), L_j)^2 + \sum_j \operatorname{ang}(\operatorname{Proj}(Y_j; K, R, T), L_j)^2$$

Where:
K is the internal calibration matrix;
$X_i$ is a vector representing the projected points from the 3D model;
$x_i$ is a vector representing the corresponding points existing on the 2D image;
Y is a vector representing the projected lines from the 3D model;
L is a vector representing the corresponding lines existing on the 2D image;
$\|\operatorname{Proj}(X_i; K, R, T) - x_i\|^2$ represents the distance error due to the points;
$\operatorname{Dis}(\operatorname{Proj}(Y_j; K, R, T), L_j)^2$ represents the distance error due to the lines; and
$\operatorname{Ang}(\operatorname{Proj}(Y_j; K, R, T), L_j)^2$ represents the angular error due to the lines.

In some other implementations, the matrix correction module 155 includes a weighting ratio between the distance error and the angular error for minimizing the projection error and calculating the final projection matrix. In such implementations, the weighting ratio may be defined, for example, by an administrator of the inspection device 130 based on the type of optimization algorithm used to calculate the final projection matrix, the type of calibration features projected, and the like. In some implementations, the matrix correction module 155 calculates the final projection matrix based on a weight-varying minimizing function. In such implementations, the matrix correction module 155 determines an optimal weighting ratio between the distance error and the angular error from a plurality of weighting ratios. Since calculating the final projection matrix using, for example, a gradient descent algorithm, is dependent on the initial projection matrix, determining an optimal weighting ratio is advantageous as it ensures that the projection error is minimized to a global minimum instead of a local minimum.

The back-projection module 160 includes codes and routines configured to project one or more measurement features from the image of the object onto a 3D model of the object. A measurement feature may be any feature of the object that is to be inspected by the inspection device 130. In some implementations, the back-projection module 160 includes a set of instructions executable by the processor 180 to provide the functionality for projecting a measurement feature from an image of the object onto a 3D model of the object. In some other implementations, the back-projection module 160 is stored in the memory 190 and is accessible and executable by the processor 180. In either implementation, the back-projection module 160 is adapted for communication and cooperation with the processor 180 and other modules of the inspection application 140.

The back-projection module 160 receives the image of the object and the final projection matrix from the communication module 145 and the matrix correction module 155 respectively. In some implementations, the back-projection module 160 projects the one or more measurement features from the received image onto the 3D model of the object based on the final projection matrix. The back-projection module 160 determines one or more differences between the projected measurement features and the corresponding measurement features existing on the 3D model of the object. For example, the back-projection module 160 projects a line representing one side (i.e., measurement feature) of a turbine blade from the received image onto a 3D model of the turbine blade. The back-projection module 160 calculates the difference between the length of the projected line and the length of the existing line representing the side of the turbine blade on the 3D model. In a further example, the back-projection module 160 also determines the distance and the angle between the projected line and the existing line on the 3D model. The back-projection module 160 is further configured to send the one or more differences to the notification module 165.

Figure 4:
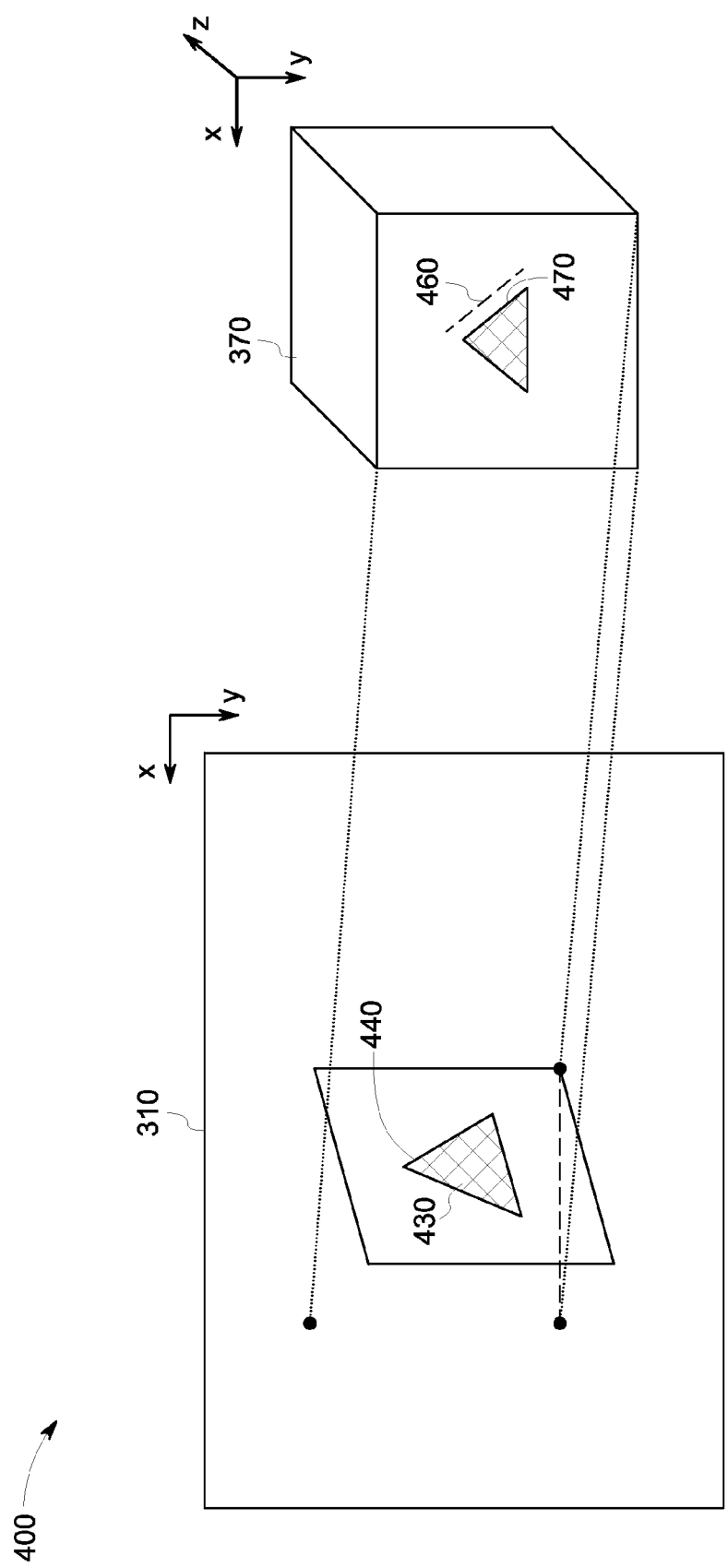
FIG. 4 is a graphical representation illustrating an example of measurement feature projections from an image of an object onto a 3D model of the object.

Referring now to FIG. 4, a graphical representation 400 of example measurement feature projections from an image 310 of an object onto a 3D model 370 of the object is illustrated in accordance with FIG. 3. The back-projection module projects a line 440 (i.e., measurement feature) of the triangular mesh 430 from the image 310 onto the 3D model 370 based on the final projection matrix. The back-projection module then determines one or more differences between the projected line 460 and the existing line 470 on the 3D model 370. For example, the back-projection module determines that the Euclidean distance (i.e., the difference) between the projected line 460 and the existing line 470 as 200 pixels. In another example, in addition to projecting the line 440, the back-projection module may project the triangular mesh 430 from the image 310 onto the 3D model 370 and determine a difference in the area of the projected triangular mesh and the area of the triangular mesh existing on the 3D model 370.

Referring back to FIG. 1, the notification module 165 includes codes and routines configured to generate and send a notification including the one or more differences between the projected measurement feature and the existing measurement feature on the 3D model of the object. In some implementations, the notification module 165 includes a set of instructions executable by the processor 180 to provide the functionality for generating and sending a notification including the one or more differences. In some other implementations, the notification module 165 is stored in the memory 190 and is accessible and executable by the processor 180. In either implementation, the notification module 165 is adapted for communication and cooperation with the processor 180 and other modules of the inspection application 140.

The notification module 165 receives the one or more differences between the projected measurement features and the existing measurement features on the 3D model of the object from the back-projection module 160. The notification module 165 generates graphical data for providing a user interface including the one or more differences to, for example, an administrator of the inspection device 130. In some implementations, the notification module 165 sends the graphical data to a display device (not shown) coupled to the inspection device 130. In such implementations, the display device (not shown) renders the graphical data and displays the user interface. In some other implementations, the notification module 165 sends the notification to an administrator of the inspection device 130 via, for example, e-mail, short messaging service, a voice message, and the like.

In some implementations, the notification module 165 determines whether the difference between the projected measurement feature and the existing measurement feature on the 3D model exceeds a discrepancy threshold. The notification module 165 retrieves the discrepancy threshold from the memory 190. As mentioned above, the discrepancy threshold is defined by, for example, an administrator of the inspection device 130 based on performance requirements of the object, regulatory requirements of the object, and the like. In such implementations, the notification module 165 generates and sends the notification in response to determining that the difference exceeds the discrepancy threshold. For example, the notification module 165 receives the difference between the length of the projected line 460 (See, FIG. 4) and the existing line 470 (See, FIG. 4) as 300 pixels. The notification module 165 determines that the difference in length of 300 pixels exceeds the discrepancy threshold of 250 pixels and sends a notification to the administrator of the inspection device 130. In such an example, the notification includes the difference in length and a warning message indicating that there is a discrepancy in the dimensions of object. In another example, the notification may further include an instruction to automatically trigger a process for repairing the object, marking the object as defective and segregating the object from the supply line, and the like. In such an example, the notification module 165 sends the instruction to, for example, a repair device (not shown), a sorting machine (not shown), and the like, that are communicatively coupled with the inspection device 130.

Figure 5:
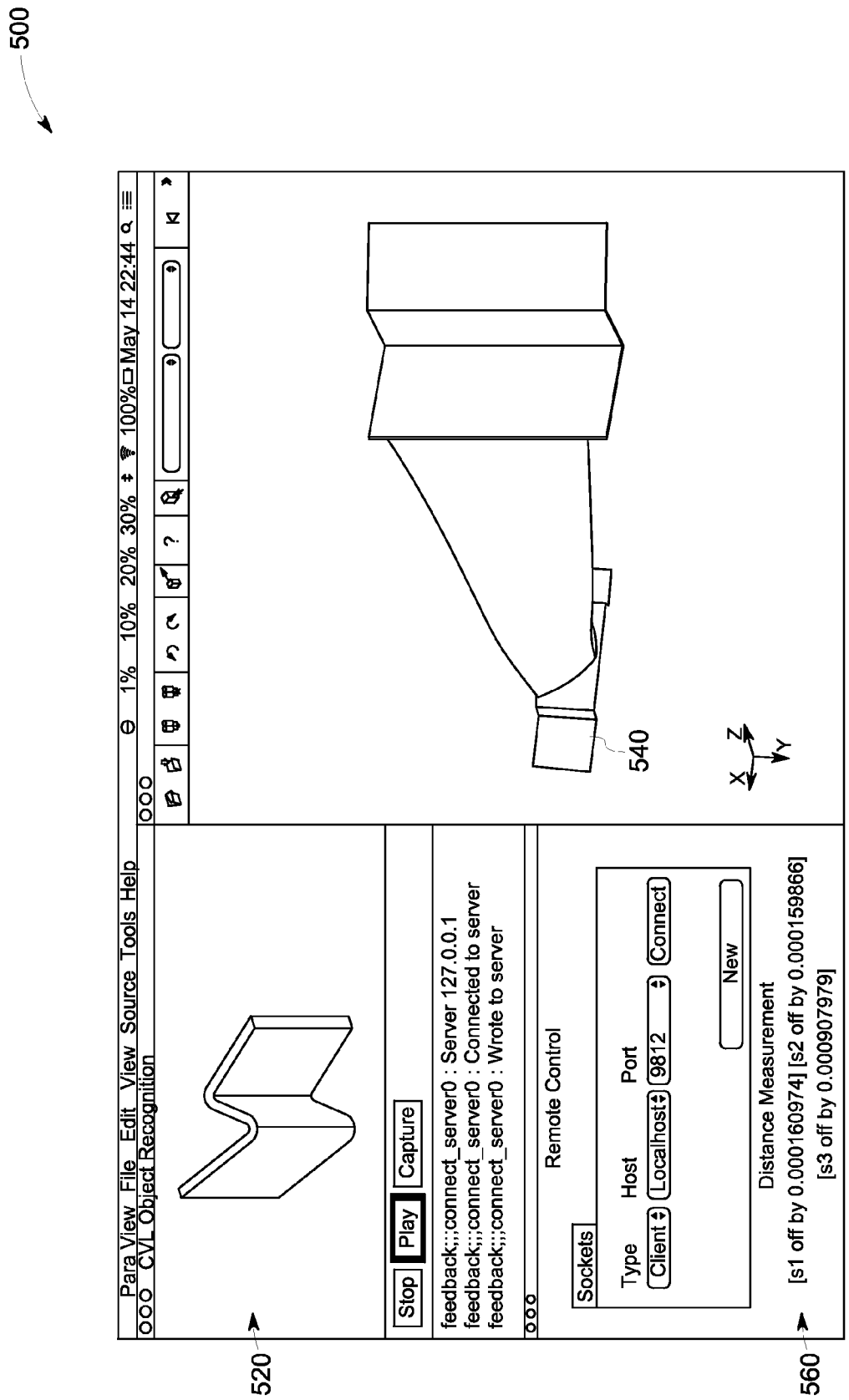
FIG. 5 is a graphical representation illustrating an example user interface including an image of an object, a 3D model of the object and differences between projected measurement features and existing measurement features on the 3D model.

Referring now to FIG. 5, a graphical representation of an example user interface 500 including an image 520 of the object, a 3D model 540 of the object and the differences 560 between projected measurement features and existing measurement features on the 3D model. The user interface 500 includes an image 520 of an aircraft's engine blade (i.e., the object) received from an image capture device. The received image 520 represents the blade with mil-level precision. In the illustrated example, the back-projection module projects three measurement features (S1, S2, and S3) from the received image 520 onto the 3D model 540 of the object based on a final projection matrix. The back-projection module determines that the difference in distance between the projected measurement feature S1 and the existing measurement feature S1 is 0.000160974 inches. Similarly, the back-projection module determines that the difference in the measurement features S2 and S3 as 0.000159866 inches and 0.000907979 inches respectively. The notification module generates graphical data for displaying a user interface 560 that includes the differences to an administrator of the inspection device.

Figure 6:
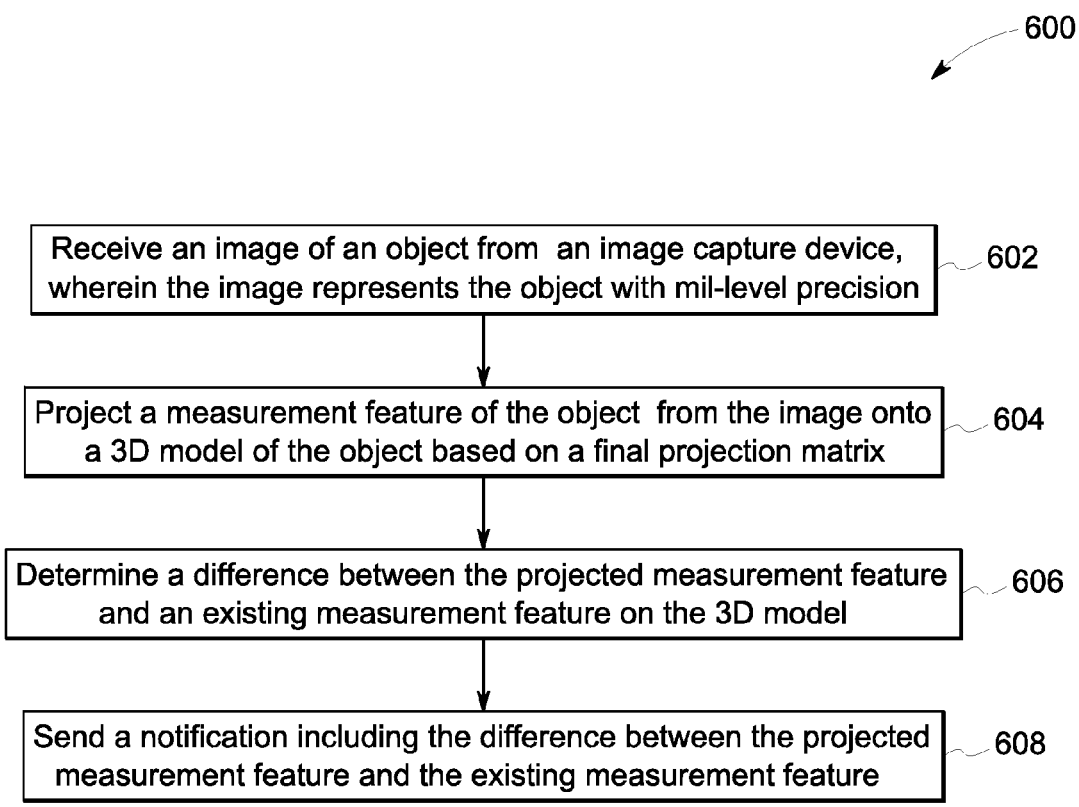
FIG. 6 is a flow diagram illustrating an example method for an image based inspection of an object.

FIG. 6 is a flow diagram illustrating an example method 600 for an image based inspection of an object. The communication module receives an image of an object from an image capture device, wherein the image represents the object with mil-level precision 602. The back-projection module projects a measurement feature of the object from the image onto a 3D model of the object based on a final projection matrix 604. The back-projection module further determines a difference between the projected measurement feature and an existing measurement feature on the 3D model 606. The notification module then sends a notification including the difference between the projected measurement feature and an existing measurement feature on the 3D model 608.

Figure 7:
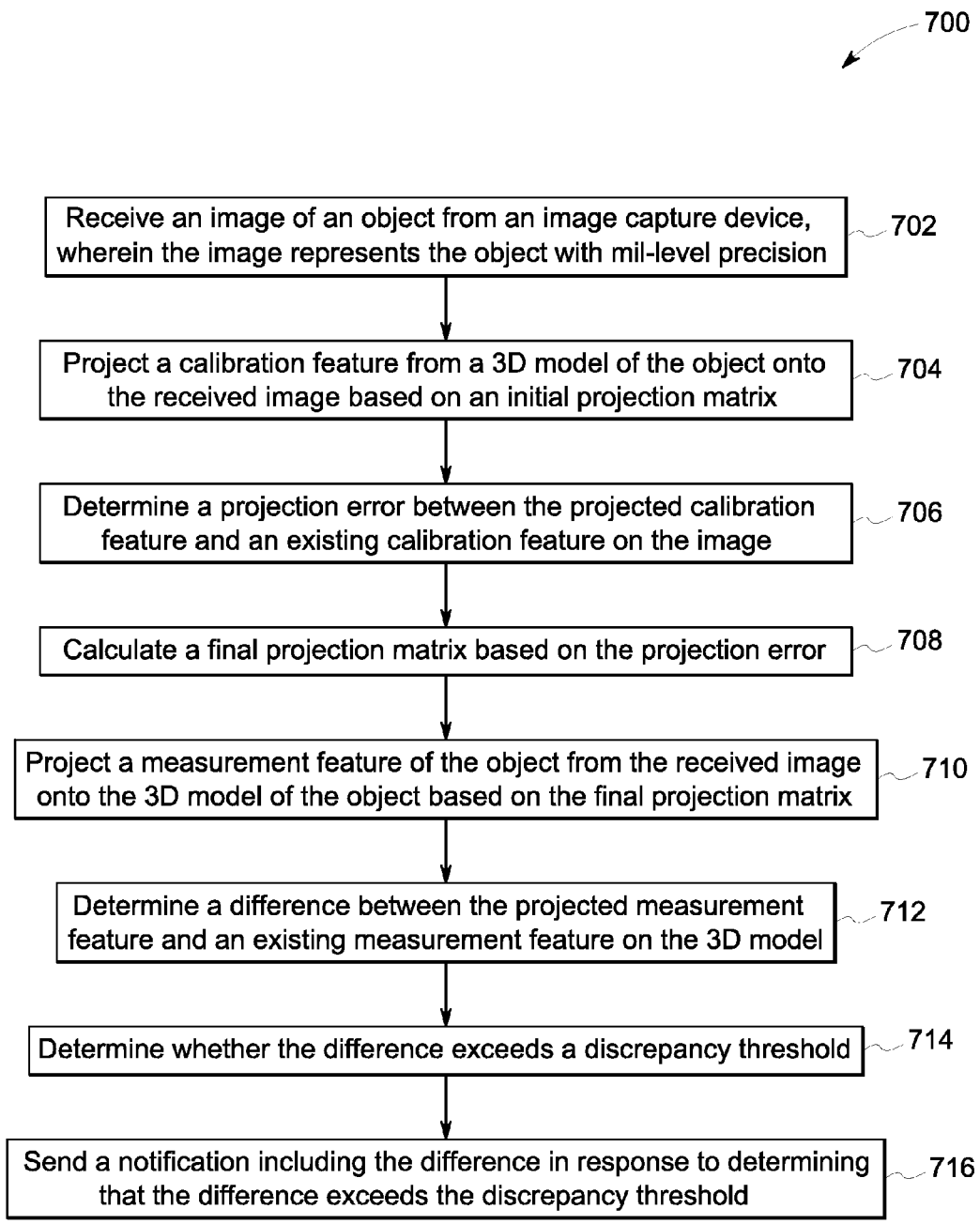
FIG. 7 is a flow diagram illustrating an example method for an image based inspection of an object.

FIG. 7 is a flow diagram illustrating an example method 700 for an image based inspection of an object. The communication module receives an image of an object from an image capture device, wherein the image represents the object with mil-level precision 702. The projection module projects a calibration feature from a 3D model of the object onto the received image based on an initial projection matrix 704. For example, the projection module projects a line from a 3D model of the object onto the received image. The projection module then determines a projection error between the projected calibration feature and an existing calibration feature on the image 706. For example, the projection module determines that the angle between projected line and the existing line on the received image is 180 degrees. The matrix correction module calculates a final projection matrix based on the projection error 708. For example, the matrix correction module calculates the final projection matrix by modifying the initial projection matrix such that the angle (i.e., the projection error) is minimized to zero using an optimization algorithm.

The back-projection module then projects a measurement feature of the object from the received image onto the 3D model of the object based on the final projection matrix 710. For example, the back-projection module projects a circle (i.e., measurement feature) from the received image onto the 3D model of the object. The back-projection module determines a difference between the projected measurement feature and an existing measurement feature on the 3D model 712. For example, the back-projection module determines a difference in the circumference of the projected circle and the existing circle as 75 units. The notification module determines whether the difference exceeds a discrepancy threshold 714. The notification module then sends a notification including the difference in response to determining that the difference exceeds the discrepancy threshold 716. For example, the notification module determines that the difference in the circumference of the circle exceeds the discrepancy threshold of 50 units and sends a notification including the difference.

It is to be understood that not necessarily all such objects or advantages described above may be achieved in accordance with any particular implementation. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the technology has been described in detail in connection with only a limited number of implementations, it should be readily understood that the invention is not limited to such disclosed implementations. Rather, the technology can be modified to incorporate any number of variations, alterations, substitutions or equivalent arrangements not heretofore described, but which are commensurate with the spirit and scope of the disclosure. Additionally, while various implementations of the technology have been described, it is to be understood that aspects of the technology may include only some of the described implementations. Accordingly, the inventions are not to be seen as limited by the foregoing description, but are only limited by the scope of the appended claims.

What is claimed as new and desired to be protected by Letters Patent of the United States is:

1. A method comprising:
    receiving an image of an object from an image capture device, wherein the image includes a representation of the object with mil-level precision;
    projecting a measurement feature of the object from the image onto a three-dimensional (3D) model of the object based on a final projection matrix;
    determining a difference between the projected measurement feature and an existing measurement feature on the 3D model;
    sending a notification including the difference between the projected measurement feature and the existing measurement feature;
    projecting a calibration feature of the object from the 3D model onto the image based on an initial projection matrix;
    determining a projection error between the projected calibration feature and an existing calibration feature on the image; and
    calculating the final projection matrix based on the projection error.

2. The method of claim 1, wherein determining the projection error further comprises determining at least one of a distance error and an angular error between the projected calibration feature and the existing calibration feature.

3. The method of claim 2, further comprising determining a weighting ratio between the distance error and the angular error.

4. The method of claim 1, wherein the initial projection matrix includes an internal calibration matrix, an initial rotational matrix, and an initial translational matrix.

5. The method of claim 4, wherein the final projection matrix includes the internal calibration, a final rotational matrix, and a final translational matrix.

6. The method of claim 1, further comprising:
    determining whether the difference between the projected measurement feature and the existing measurement feature exceeds a discrepancy threshold; and
    sending the notification to a user in response to determining that the difference exceeds the discrepancy threshold.

7. A system comprising:
    at least one processor;
    a communication module stored in a memory and executable by the at least one processor, the communication module configured to receive an image of an object from an image capture device, wherein the image includes a representation of the object with mil-level precision;
    a back-projection module stored in the memory and executable by the at least one processor, the back-projection module communicatively coupled with the communication module and configured to project a measurement feature of the object from the image onto a three-dimensional (3D) model of the object based on a final projection matrix and determine a difference between the projected measurement feature and an existing measurement feature on the 3D model;
    a notification module stored in the memory and executable by the at least one processor, the notification module communicatively coupled with the back-projection module and configured to send a notification including the difference between the projected measurement feature and the existing measurement feature; and
    a projection module configured to project a calibration feature of the Object from the 3D model onto the image based on an initial projection matrix and determine a projection error between the projected calibration feature and an existing calibration feature on the image.

8. The system of claim 7, further comprises a matrix correction module configured to calculate the final projection matrix based on the projection error.

9. The system of claim 8, wherein the matrix correction module is further configured to calculate the final projection matrix based on at least one of a distance error and an angular error between the projected calibration feature, and the existing calibration feature.

10. The system of claim 9, wherein the matrix correction module is further configured to calculate the final projection matrix based on a weighting ratio between the distance error and the angular error.

11. The system of claim 7, wherein the initial projection matrix includes an internal calibration matrix, an initial rotational matrix, and an initial translational matrix.

12. The system of claim 11, wherein the final projection matrix includes the internal calibration matrix, a final rotational matrix, and a final translational matrix.

13. The system of claim 7, wherein the notification module is further configured to determine whether the difference between the projected measurement feature and the existing measurement feature exceeds a discrepancy threshold and send the notification to a user in response to determining that the difference exceeds the discrepancy threshold.

14. A computer program product comprising a non-transitory computer readable physical storage device encoding instructions that, in response to execution by at least one processor, cause the processor to perform operations comprising:
   receive an image of an object from an image capture device, wherein the image includes a representation of the object with mil-level precision;
   project a measurement feature of the object from the image onto a three-dimensional (3D) model of the object based on a final projection matrix;
   determine a difference between the projected measurement feature and an existing measurement feature on the 3D model;
   send a notification including the difference between the projected measurement feature and the existing measurement feature;
   project a calibration feature of the object from the 3D model onto the image based on an initial projection matrix;
   determine a projection error between the projected calibration feature and an existing calibration feature on the image; and
   calculate the final projection matrix based on the projection error.

15. The computer program product of claim 14, further causing, the processor to determine at least one of a distance error and an angular error between the projected calibration feature and the existing calibration feature.

16. The computer program product of claim 15, further causing the processor to determine a weighting ratio between the distance error and the angular error.

17. The computer program product of claim 14, further causing the processor to perform operations comprising:
   determine whether the difference between the projected measurement feature and the existing measurement feature exceeds a discrepancy threshold; and
   send the notification to a user in response to determining that the difference exceeds the discrepancy threshold.

* * * * *